United States Patent
Hoge, II (10) Patent No.: US 7,390,931 B2
(45) Date of Patent: Jun. 24, 2008

(54) PREPARATION OF P-CHIROGENIC PHOSPHOLANES AND THEIR USE IN ASYMMETRIC SYNTHESIS

(75) Inventor: Garrett Stewart Hoge, II, Ann Arbor, MI (US)

(73) Assignee: Pfizer Inc., New York, NY (US)

(*) Notice: Subject to any disclaimer, the term of this patent is extended or adjusted under 35 U.S.C. 154(b) by 269 days.

(21) Appl. No.: 11/095,044

(22) Filed: Mar. 31, 2005

(65) Prior Publication Data

US 2005/0222464 A1    Oct. 6, 2005

Related U.S. Application Data

(60) Provisional application No. 60/559,043, filed on Apr. 1, 2004.

(51) Int. Cl.
C07F 9/02    (2006.01)

(52) U.S. Cl. .......................................................... 568/12
(58) Field of Classification Search ................. 568/12
See application file for complete search history.

(56) References Cited

U.S. PATENT DOCUMENTS

| | | | |
|---|---|---|---|
| 5,563,175 | A | 10/1996 | Silverman et al. |
| 6,001,876 | A | 12/1999 | Singh |
| 6,127,418 | A | 10/2000 | Bueno et al. |
| 6,194,459 | B1 | 2/2001 | Akunne et al. |
| 6,242,488 | B1 | 6/2001 | Bueno et al. |
| 6,306,910 | B1 | 10/2001 | Magnus et al. |
| 6,326,374 | B1 | 12/2001 | Magnus et al. |
| 6,329,429 | B1 | 12/2001 | Schrier et al. |
| 6,359,005 | B1 | 3/2002 | Pande |
| 6,426,368 | B2 | 7/2002 | Bueno et al. |
| 6,605,745 | B2 | 8/2003 | Hoge et al. |
| 2002/0870717 | | 7/2002 | Hoge et al. |

OTHER PUBLICATIONS

Berge et al., "Pharmaceutical Salts," J. of Pharm.Sci., (1977), vol. 66, pp. 1-19.
Brunner, "Enantioselective Synthesis with Optically Active Transition-Metal Catalysts", (1988), pp. 645-654.
Brunner et al., "Synthesis of New Optically Active Bis- and Tris(phosphines), Synthesis", (1989), pp. 706-709.
Cai et al., "Synthesis of CMI-977, a Potent 5-Lipoxygenase Inhibitor", Organic Process Research and Development, (1999), pp. 73-76, vol. 3.
Cremer et al., Pyramidal Inversion in Substituted Phoshetanes:, Tetrahedron Letters, (1968), pp. 5799-5802, vol. 55.
Egan et al., "The Low Barrier to Pyramidal Inversion in Phosholes, A Measure of Aromaticity", J. Am. Chem., (1970), pp. 1442-1444, vol. 92.

(Continued)

*Primary Examiner*—Rei-tsang Shiao
(74) *Attorney, Agent, or Firm*—Robert N. Young; Suzanne M. Harvey; Scott A. Williams (57) ABSTRACT

Materials and methods for preparing P-chirogenic monophospholanes and bisphospholanes are disclosed. The methods employ stereoselective cyclization to generate the phospholane rings followed by pyramidal inversion to access a variety of P-chirogenic phospholanes. When bound to transition metals such as rhodium, the disclosed P-chirogenic phospholanes may be used as catalysts in asymmetric synthesis of valuable pharmaceutical chemical entities, including pregabalin.

20 Claims, 3 Drawing Sheets

OTHER PUBLICATIONS

Herdeis, "Chirospecific Synthesis of (S)-(+)- and (R)-(−)-5-Amino-4-hydroxypentanoic Acid from L- and D-Glutamic Acid via (S)-(+)- and (R)-(−)-5-Hydroxy-2-oxopiperidine" Synthesis, (1986), pp. 232-234.

Hoge, Synthesis of Both Enantiomers of a P-Chirogenic 1,2-Bisphospholanoethane Ligand via Convergent Routes and Application to Rhodium-Catalyzed Asymmetric Hydrogenation of CI-1008 (Pregabalin), J. Am. Chem. Soc., (2003), pp. 10219-10227, vol. 125.

Hommer et al., "Synthesis and study of the thermal epimerization of r-2-ethoxy-cis-4-cis-5-dimethyl- . . . ", Phosphorous, Sulfur, and Silicon, (2002), pp. 465-470, vol. 177.

Knowles et al., "Asymmetric Hydrogenation with a Complex of Rhodium and Chiral Bisphosphine", J. Am. Chem. Soc., (1975), pp. 2567-2568, vol. 97(9).

Lambert, "Pyramidal Atomic Inversion", Topics in Stereochemistry, (1971), pp. 19-105, vol. 6.

Mori, "Synthesis of Optically Active Forms of Sulcatol", Tetrahedron, (1975), pp. 3011-3012, vol. 31.

Nemoto et al., "Synthetic Approach to (+)-Aldosterone and Its Relatives", J. Org. Chem., (1985), pp. 2764-2766, vol. 50.

Noyori et al., Modern Synthetic Methods, (1989), pp. 115-198, vol. 5.

Nugent et al., "Beyon Nature's Chiral Pool: Enantioselective Catalysis in Industry", Science, (1993), pp. 479-483, vol. 259.

Rauk et al., "Pyramidal Inversion", Angew. Chem. International Edition, (1970), pp. 400-414, vol. 9.

Ravid et al., "Synthesis of the Evantiomers of 4-Substituted . . . " Tetrahedron, (1978), pp. 1449-1452, vol. 34.

Vedejs et al., "2-Aryl-4,4,8-trimethyl-2-phosphabicyclo[3.3.0]octanes: Reactive Chrial Phosphine Catalysts for Enantioselcective Acylation", J. Am. Chem. Soc., (1999), pp. 5813-5814, vol. 121.

Vedejs et al., "A Highly Enanthiselective Phosphabicyclooctane Catalyst for the Kinetic Resolution of Benzylic Alcohols", J. Am. Chem. Soc., (2003), pp. 4166-4173, vol. 125.

Vineyard et al., "Symmetric Hydrogenation. Rhodium Chiral Bisphosphine Catalyst", J. Am. Chem. Soc., (1977), pp. 5945-5952, vol. 99(18).

Borleske, S.G. et al., "Carboxy Derivatives of Five-Membered Cyclic Phosphorus Compounds", Phosphorus Sulfur and The Related Elements, (1975), vol. 3, pp. 173-182.

Hoge, G., "Stereoselective Cyclization and Pyramidal Inversion Strategies for P-Chirogenic Phospholane Synthesis", J. of Amer. Chem. Society, (2004), vol. 126, pp. 9920-9921.

PREPARATION OF P-CHIROGENIC PHOSPHOLANES AND THEIR USE IN ASYMMETRIC SYNTHESIS

CROSS-REFERENCE TO RELATED APPLICATION

This application claims the benefit of U.S. Provisional Application No. 60/559,043, filed Apr. 1, 2004, the complete disclosure of which is herein incorporated by reference.

BACKGROUND OF THE INVENTION

1. Field of the Invention

This invention relates to materials and methods for preparing P-chirogenic phospholane ligands and to their use in asymmetric syntheses, including the enantioselective hydrogenation of prochiral olefins to prepare pharmaceutically useful compounds such as pregabalin.

2. Discussion

Asymmetric catalysis is often the most efficient method for the synthesis of enantiomerically enriched compounds because a small amount of a chiral catalyst can be used to produce a large quantity of a chiral target molecule. Over the last two decades, more than a half-dozen commercial industrial processes have been developed that use asymmetric catalysis as the key step in the production of enantiomerically pure compounds with much effort focused on developing new asymmetric catalysts for these reactions. See, e.g., J. D. Morrison, ed., *Asymmetric Synthesis* 5 (1985); B. Bosnich, ed., *Asymmetric Catalysis* (1986); H. Brunner, *Synthesis* 645 (1988); R. Noyori & M. Kitamura, in R. Scheffold, ed., *Modern Synthetic Methods* 5:115 (1989); W. A. Nugent et al., *Science* 259:479 (1993); I. Ojima, ed., *Catalytic Asymmetric Synthesis* (1993); R. Noyori, *Asymmetric Catalysis In Organic Synthesis* (1994). For more recent examples, see "Special Feature Section: Homogeneous Transition Metal-Catalyzed Reactions," *Organic Process Research and Development* 7 (3):341-445 (2003).

Chiral phosphine ligands have played a significant role in the development of novel transition metal catalyzed asymmetric reactions to produce enantiomeric excess of compounds with desired activities. The first successful attempts at asymmetric hydrogenation of eneamide substrates were accomplished in the late 1970s using chiral bisphosphines as transition metal ligands. See, e.g., B. D. Vineyard et al., *J. Am. Chem. Soc.* 99 (18):5946-52 (1977); W. S. Knowles et al., *J. Am. Chem. Soc.* 97 (9):2567-68 (1975). Since these first published reports, there has been a continuous expansion of research related to the synthesis of new chiral bisphosphine ligands for asymmetric hydrogenations and other chiral catalytic transformations. See I. Ojima, ed., *Catalytic Asymmetric Synthesis* (1993); D. J. Ager, ed., *Handbook of Chiral Chemicals* (1999).

Much of the current interest in new chiral ligands and catalysts results from their use in preparing enantiomerically enriched or enantiopure drugs. One such drug is pregabalin, (S)-3-aminomethyl-5-methyl-hexanoic acid, which is the active pharmaceutical ingredient in LYRICA®. Pregabalin is related to the endogenous inhibitory neurotransmitter γ-aminobutyric acid (GABA), which is involved in the regulation of brain neuronal activity. Pregabalin exhibits anti-seizure activity, as described in U.S. Pat. No. 5,563,175 to R. B. Silverman et al., and is thought to be useful for treating, among other conditions, pain, physiological conditions associated with psychomotor stimulants, inflammation, gastrointestinal damage, alcoholism, insomnia, and various psychiatric disorders, including mania and bipolar disorder. See, respectively, U.S. Pat. No. 6,242,488 to L. Bueno et al., U.S. Pat. No. 6,326,374 to L. Magnus & C. A. Segal, and U.S. Pat. No. 6,001,876 to L. Singh; U.S. Pat. No. 6,194,459 to H. C. Akunne et al.; U.S. Pat. No. 6,329,429 to D. Schrier et al.; U.S. Pat. No. 6,127,418 to L. Bueno et al.; U.S. Pat. No. 6,426,368 to L. Bueno et al.; U.S. Pat. No. 6,306,910 to L. Magnus & C. A. Segal; and U.S. Pat. No. 6,359,005 to A. C. Pande, which are herein incorporated by reference in their entirety and for all purposes.

A recent U.S. patent describes a method of making pregabalin and other chiral compounds via asymmetric hydrogenation of a cyano-substituted olefin to produce a chiral cyano precursor of (S)-3-aminomethyl-5-methyl-hexanoic acid. See U.S. Pat. No. 6,605,745 to G. S. Hoge, II & O. P. Goel (the '745 patent), which is assigned to the Warner-Lambert Company LLC and is herein incorporated by reference in its entirety for all purposes. The cyano precursor is subsequently reduced to give enantiomerically-enriched pregabalin in high yield. According to the '745 patent, the asymmetric hydrogenation employs a chiral catalyst, which is comprised of a transition metal (e.g., rhodium) bound to a P-chirogenic bisphospholane ligand, such as 1,2-bis((1R,2R)-2-benzylphospholanyl)ethane, Besides alkanediyls, such as the ethanediyl in Formula 1, the '745 patent discloses other bridges that link the phosphorus atoms, including substituted and unsubstituted phen-1,2-diyl bridges as shown in the compound of Formula 2, The '745 patent discloses numerous methods for making P-chirogenic bisphospholane ligands. One useful method employs a CuCl$_2$ promoted oxidative coupling of a methyl anion of the compound of Formula 3,

3 which is obtained by treating the compound of Formula 3 with a strong base, such as s-BuLi. Although this approach is useful for preparing P-chirogenic bisphospholanes similar to the compound of Formula 1, such approaches are less useful for ligands exemplified by Formula 2. Therefore, it would be desirable to develop a general technique for preparing P-chirogenic bisphospholanes.

SUMMARY OF THE INVENTION

The present invention provides materials and methods for preparing P-chirogenic monophospholanes (Formula 9) and bisphospholanes (Formula 10) via stereoselective cyclization of a phosphine precursor (Formula 6) to generate the phospholane rings. Pyramidal inversion of the phosphine moieties permits access to a variety of P-chirogenic phospholane diastereoisomers. When bound to transition metals such as rhodium, the disclosed P-chirogenic phospholanes may be used as catalysts in asymmetric synthesis of valuable pharmaceutical chemical entities, including pregabalin.

One aspect of the present invention provides a method of making compounds of Formula 9,

9 or Formula 10,

10 or opposite enantiomers thereof, wherein
R is C$_{1-6}$ alkyl, halo-C$_{1-6}$ alkyl, C$_{3-8}$ cycloalkyl, halo-C$_{3-8}$ cycloalkyl, alkanoyl, C$_{1-6}$ alkoxy, C$_{1-6}$ alkoxy-C$_{1-6}$ alkyl, C$_{1-6}$ alkoxycarbonyl, aryl, aryl-C$_{1-6}$ alkyl, aryloxy, aryl-C$_{1-6}$ alkoxy, aryloxycarbonyl, aryl-C$_{1-6}$ alkoxycarbonyl, or carboxy, and each of the aryl and the C$_{3-8}$ cycloalkyl moieties are independently substituted or unsubstituted, and
X is C$_{1-12}$ alkyl, C$_{1-12}$ alkanediyl, or phen-1,2-diyl, in which phen-1,2-diyl is substituted or unsubstituted, the method comprising epimerizing compounds of Formula 7,

7 or Formula 8,

8 or opposite enantiomers thereof, to give the compounds of Formula 9, or Formula 10, or the opposite enantiomers thereof, respectively, wherein R and X in Formula 7 and Formula 8 are as defined in Formula 9 and Formula 10.

In the claimed method, epimerizing the compounds typically comprises heating a reaction mixture containing the compounds of Formula 7 or Formula 8 or opposite enantiomers thereof, at a temperature greater than or about equal to 100° C. and less than or about equal to the decomposition temperature of the compounds of Formula 7 or Formula 8, which is typically about 250° C. This corresponds to heating the reaction mixture at a temperature greater than or about equal to 100° C., 110° C., 120° C., 130° C., 140° C., 150° C., 160° C., 170° C., 180° C., 190° C., 200° C., 210° C., 220° C., 230° C., 240° C. or 250° C. and less than or about equal to 110° C., 120° C., 130° C., 140° C., 150° C., 160° C., 170° C., 180° C., 190° C., 200° C., 210° C., 220° C., 230° C., 240° C., or 250° C. In some cases, epimerizing the compounds comprises heating a reaction mixture containing the compounds of Formula 7 or Formula 8 or opposite enantiomers thereof, at a temperature greater than or about equal to 140° C. and less than or about equal to 210° C. or at a temperature greater than or about equal to 190° C. and less than or about equal to 210° C.

In the claimed method, the compounds of Formula 7 or Formula 8 or their opposite enantiomers, are generally epimerized in the absence of oxygen or when the reaction mixture contains less than about 1%, 0.1%, or 0.01% of oxygen by mass.

Another aspect of the present invention provides a method of making compounds of Formula 7,

7 or Formula 8, or opposite enantiomers thereof, wherein R and X are as defined above in Formula 9 and Formula 10, the method comprising:
(a) treating a compound of Formula 6, X(PH$_2$)$_n$                                                   6, with a first base to generate a first intermediate, wherein n in Formula 6 is 1 or 2 and X is as defined in Formula 9 and Formula 10;
(b) reacting the first intermediate with a compound of Formula 5, or an opposite enantiomer thereof, to yield a second intermediate; and
(c) treating the second intermediate with a second base to yield the compounds of Formula 7, or Formula 8, or opposite enantiomers thereof, wherein R in Formula 5 is as defined in Formula 7 and Formula 8, and the first and second bases are the same or different.

In the methods for preparing compounds of Formula 7 to Formula 10, R is typically $C_{1-6}$ alkyl, $C_{1-6}$ alkoxy-$C_{1-6}$ alkyl, or aryl-$C_{1-6}$ alkyl, and X is typically $C_{1-6}$ alkyl, $C_{1-2}$ alkanediyl, or phen-1,2-diyl. Useful R thus include methyl, ethyl, isopropyl, methoxymethyl, or benzyl, and useful X include methyl, methylene, ethanediyl, or phen-1,2-diyl.

An additional aspect of the present invention provides compounds of Formula 7, or Formula 8, or opposite enantiomers thereof, wherein R and X are as defined above in Formula 9 and Formula 10, and provided that R in Formula 7 is not methyl.

A further aspect of the present invention provides compounds of Formula 11, or Formula 12, or opposite enantiomers thereof, wherein R and X are as defined above in Formula 9 and Formula 10, and provided that R in Formula 11 is not methyl.

Another aspect of the present invention provides compounds of Formula 5, or opposite enantiomers thereof, wherein R is as defined above in Formula 9 and Formula 10.

In each of the compounds of Formula 5 and Formula 7, 8, 11, and 12, R is typically $C_{1-6}$ alkyl, $C_{1-6}$ alkoxy-$C_{1-6}$ alkyl, or aryl-$C_{1-6}$ alkyl, and X is typically $C_{1-6}$ alkyl, $C_{1-2}$ alkanediyl, or phen-1,2-diyl. Subject to the provisos regarding compounds of Formula 7 and Formula 11, useful R thus include methyl, ethyl, isopropyl, methoxymethyl, or benzyl, and useful X include methyl, methylene, ethanediyl, or phen-1,2-diyl. Particularly useful compounds include:
(4S)-4-benzyl-1,3,2-dioxathiepane 2,2-dioxide;
(4R)-4-methyl-1,3,2-dioxathiepane 2,2-dioxide;
(4S)-4-(methoxymethyl)-1,3,2-dioxathiepane 2,2-dioxide;
(1R,2R)-1-phenyl-2-benzylphospholane;
(1R,2R)-1-phenyl-2-(methoxymethyl)phospholane;
1,2-bis((1R,2R)-2-benzylphospholano)benzene;
1,2-bis((1R,2S)-2-methylphospholano)benzene;
1,2-bis((1S,2R)-2-benzylphospholano)ethane;
(1S,2R)-1-phenyl-2-(methoxymethyl)phospholane;
(1S,2R)-1-phenyl-2-benzylphospholane;
1-((1R,2S)-2-methylphospholan-1-yl)-2-((1S,2S)-2-methylphospholan-1-yl) -benzene;
1-((1R,2R)-2-benzylphospholan-1-yl)-2-((1S,2R)-2-benzylphospholan-1-yl) -benzene;
1-((1R,2R)-2-benzylphospholan-1-yl)-2-((1S,2R)-2-benzylphospholan-1-yl) -ethane;

opposite enantiomers thereof; and complexes, salts, solvates or hydrates thereof.

The scope of the present invention includes all complexes, salts, solvates, hydrates, polymorphs, esters, amides, and prodrugs of the claimed and disclosed compounds, including compounds of Formula 5, 7, 8, 11, and 12, whether pharmaceutically acceptable or not.

DETAILED DESCRIPTION

Definitions and Abbreviations

Unless otherwise indicated, this disclosure uses definitions provided below. Some of the definitions and formulae may include a "-" (dash) to indicate a bond between atoms or a point of attachment to a named or unnamed atom or group of atoms. Other definitions and formulae may include an "=" (equal sign) or "≡" (identity sign) to indicate a double bond or a triple bond, respectively.

"Substituted" groups are those in which one or more hydrogen atoms have been replaced with one or more non-hydrogen groups, provided that valence requirements are met and that a chemically stable compound results from the substitution.

"Alkyl" refers to straight chain and branched saturated hydrocarbon groups, generally having a specified number of carbon atoms (i.e., $C_{1-6}$ alkyl refers to an alkyl group having 1, 2, 3, 4, 5, or 6 carbon atoms). Examples of alkyl groups include, without limitation, methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more unsaturated carbon-carbon bonds, and generally having a specified number of carbon atoms. Examples of alkenyl groups include, without limitation, ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms. Examples of alkynyl groups include, without limitation, ethynyl, 1-propyn-1-yl, 2-propyn-1-yl, 1-butyn-1-yl, 3-butyn-1-yl, 3-butyn-2-yl, 2-butyn-1-yl, and the like.

"Alkanediyl" refers to divalent straight chain and branched aliphatic hydrocarbon groups, generally having a specified number of carbon atoms. Examples include, without limitation, methylene, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl, and the like.

"Phenyl-1,2-diyl" refers to a divalent phenyl group, which is bonded to a parent group or substrate via adjacent ring carbon atoms.

"Alkanoyl" and "alkanoylamino" refer, respectively, to alkyl-C(O)— and alkyl-C(O)—NH—, where alkyl is defined above, and generally includes a specified number of carbon atoms, including the carbonyl carbon. Examples of alkanoyl groups include, without limitation, formyl, acetyl, propionyl, butyryl, pentanoyl, hexanoyl, and the like.

"Alkoxy," "alkoxyalkyl," "alkoxycarbonyl," and "alkoxycarbonylamino," refer, respectively, to alkyl-O—, alkyl-O-alkyl, alkyl-O—C(O)—, and alkyl-O—C(O)—NH—, where alkyl is defined above. Examples of alkoxy groups include, without limitation, methoxy, ethoxy, n-propoxy, i-propoxy, n-butoxy, s-butoxy, t-butoxy, n-pentoxy, s-pentoxy, and the like.

"Alkylamino," "alkylaminocarbonyl," "dialkylaminocarbonyl," "alkylsulfonyl" "sulfonylaminoalkyl," and "alkylsulfonylaminocarbonyl" refer, respectively, to alkyl-NH—, alkyl-NH—C(O)—, alkyl$_2$-N—C(O)—, alkyl-S(O$_2$)—, HS(O$_2$)—NH-alkyl-, and alkyl-S(O)—NH—C(O)—, where alkyl is defined above.

"Aminoalkyl" and "cyanoalkyl" refer, respectively, to NH$_2$-alkyl and N≡C-alkyl, where alkyl is defined above.

"Cycloalkyl" refers to saturated monocyclic and bicyclic hydrocarbon rings, generally having a specified number of carbon atoms that comprise the ring (i.e., $C_{3-7}$ cycloalkyl refers to a cycloalkyl group having 3, 4, 5, 6 or 7 carbon atoms as ring members). The cycloalkyl may be attached to a parent group or to a substrate at any ring atom, unless such attachment would violate valence requirements. Likewise, the cycloalkyl groups may include one or more non-hydrogen substituents unless such substitution would violate valence requirements. Useful substituents include, without limitation, alkyl, alkoxy, alkoxycarbonyl, and alkanoyl, as defined above, and hydroxy, mercapto, nitro, halogen, and amino.

Examples of monocyclic cycloalkyl groups include, without limitation, cyclopropyl, cyclobutyl, cyclopentyl, cyclohexyl, and the like. Examples of bicyclic cycloalkyl groups include, without limitation, bicyclo[1.1.0]butyl, bicyclo[1.1.1]pentyl, bicyclo[2.1.0]pentyl, bicyclo[2.1.1]hexyl, bicyclo[3.1.0]hexyl, bicyclo[2.2.1]heptyl, bicyclo[3.2.0]heptyl, bicyclo[3.1.1]heptyl, bicyclo[4.1.0]heptyl, bicyclo[2.2.2]octyl, bicyclo[3.2.1]octyl, bicyclo[4.1.1]octyl, bicyclo[3.3.0]octyl, bicyclo[4.2.0]octyl, bicyclo[3.3.1]nonyl, bicyclo[4.2.1]nonyl, bicyclo[4.3.0]nonyl, bicyclo[3.3.2]decyl, bicyclo[4.2.2]decyl, bicyclo[4.3.1]decyl, bicyclo[4.4.0]decyl, bicyclo[3.3.3]undecyl, bicyclo[4.3.2]undecyl, bicyclo[4.3.3]dodecyl, and the like.

"Cycloalkanoyl" refers to cycloalkyl-C(O)—, where cycloalkyl is defined above, and generally includes a specified number of carbon atoms, excluding the carbonyl carbon. Examples of cycloalkanoyl groups include, without limitation, cyclopropanoyl, cyclobutanoyl, cyclopentanoyl, cyclohexanoyl, cycloheptanoyl, and the like.

"Halo," "halogen" and "halogeno" may be used interchangeably, and refer to fluoro, chloro, bromo, and iodo.

"Haloalkyl," "halocycloalkyl," and "haloalkanoyl" refer, respectively, to alkyl, cycloalkyl, or alkanoyl groups substituted with one or more halogen atoms, where alkyl, cycloalkyl, and alkanoyl are defined above. Examples of haloalkyl and haloalkanoyl groups include, without limitation, trifluoromethyl, trichloromethyl, pentafluoroethyl, pentachloroethyl, trifluoroacetyl, trichloroacetyl, pentafluoropropionyl, pentachloropropionyl, and the like.

"Hydroxyalkyl" and "oxoalkyl" refer, respectively, to HO-alkyl and O=alkyl, where alkyl is defined above. Examples of hydroxyalkyl and oxoalkyl groups, include, without limitation, hydroxymethyl, hydroxyethyl, 3-hydroxypropyl, oxomethyl, oxoethyl, 3-oxopropyl, and the like.

"Aryl" and "arylene" refer to monovalent and divalent aromatic groups, respectively. Examples of aryl groups include, without limitation, phenyl, naphthyl, biphenyl, pyrenyl, anthracenyl, fluorenyl, and the like, which may be unsubstituted or substituted with 1 to 4 substituents. Such substituents include, without limitation, alkyl, alkoxy, alkoxycarbonyl, alkanoyl, and cycloalkanoyl, as defined above, and hydroxy, mercapto, nitro, halogen, and amino.

"Arylalkyl" refers to aryl-alkyl, where aryl and alkyl are defined above. Examples include, without limitation, benzyl, fluorenylmethyl, and the like.

"Arylalkanoyl" refers to aryl-alkanoyl, where aryl and alkanoyl are defined above. Examples include, without limitation, benzoyl, phenylethanoyl, phenylpropanoyl, and the like.

"Aryloxy" refers to aryl-O—, where aryl is defined above. Examples include, without limitation, phenoxy and the like.

"Aryloxycarbonyl" refers to aryl-O—C(O)—, where aryl is defined above. Examples include, without limitation, phenoxycarbonyl and the like.

"Arylalkoxy" refers to aryl-alkoxy, where aryl and alkoxy are defined above. Examples of arylalkoxy include, without limitation, benzyloxy, fluorenylmethoxy, and the like.

"Arylalkoxycarbonyl" refers to aryl-alkoxycarbonyl, where aryl and alkoxycarbonyl are defined above. Examples include, without limitation, phenoxycarbonyl, benzyloxycarbonyl (CBz), and the like.

"Carboxy" refers to HOOC—.

"Heterocycle" and "heterocyclyl" refer to saturated, partially unsaturated, or unsaturated monocyclic or bicyclic rings having from 5 to 7 or from 7 to 11 ring members, respectively. These groups have ring members made up of carbon atoms and from 1 to 4 heteroatoms that are independently nitrogen, oxygen or sulfur, and may include any bicyclic group in which any of the above-defined monocyclic heterocycles are fused to a benzene ring. The nitrogen and sulfur heteroatoms may optionally be oxidized. The heterocyclic ring may be attached to a parent group or to a substrate at any heteroatom or carbon atom unless such attachment would violate valence requirements. Likewise, any of the carbon or nitrogen ring members may include a non-hydrogen substituent unless such substitution would violate valence requirements. Useful substituents include, without limitation, alkyl, alkoxy, alkoxycarbonyl, alkanoyl, and cycloalkanoyl, as defined above, and hydroxy, mercapto, nitro, halogen, and amino.

Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heteroaryl" and "heteroarylene" refer, respectively, to monovalent and divalent heterocycles or heterocyclyl groups, as defined above, which are aromatic. Heteroaryl and heteroarylene groups represent a subset of aryl and arylene groups, respectively.

"P-chirogenic" refers to a molecule having at least one phosphorus atom that is a stereocenter.

"Phospholane ring" refers to a 5-membered cyclic structure in which at least one atom is phosphorous.

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, and nosylate). Others include carbonates, halide ions, carboxylate anions, phenolate ions, and alkoxides. Some stronger bases, such as $NH_2^-$ and $OH^-$ can be made better leaving groups by treatment with an acid. Common electrofugal leaving groups include the proton, $CO_2$, and metals.

"Enantiomeric excess" or "ee" is a measure, for a given sample, of the excess of one enantiomer over a racemic sample of a chiral compound and is expressed as a percentage. Enantiomeric excess is defined as $100\times(er-1)/(er+1)$, where "er" is the ratio of the more abundant enantiomer to the less abundant enantiomer.

"Diastereomeric excess" or "de" is a measure, for a given sample, of the excess of one diastereomer over a sample having equal amounts of diastereomers and is expressed as a percentage. Diastereomeric excess is defined as $100\times(dr-1)/(dr+1)$, where "dr" is the ratio of a more abundant diastereomer to a less abundant diastereomer.

"Stereoselective," "enantioselective," "diastereoselective," and variants thereof, refer to a given process (e.g., hydrogenation) that yields more of one stereoisomer, enantiomer, or diastereoisomer than of another, respectively.

"High level of stereoselectivity," "high level of enantioselectivity," "high level of diastereoselectivity," and variants thereof, refer to a given process that yields products having an excess of one stereoisomer, enantiomer, or diastereoisomer, which comprises at least about 90% of the products. For a pair of enantiomers or diastereomers, a high level of enantioselectivity or diastereoselectivity would correspond to an ee or de of at least about 80%.

"Stereoisomerically enriched," "enantiomerically enriched," "diastereomerically enriched," and variants thereof, refer, respectively, to a sample of a compound that has more of one stereoisomer, enantiomer or diastereomer than another. The degree of enrichment may be measured by % of total product, or for a pair of enantiomers or diastereomers, by ee or de.

"Substantially pure stereoisomer," "substantially pure enantiomer," "substantially pure diastereomer," and variants thereof, refer, respectively, to a sample containing a stereoisomer, enantiomer, or diastereomer, which comprises at least about 95% of the sample. For pairs of enantiomers and diastereomers, a substantially pure enantiomer or diastereomer would correspond to samples having an ee or de of about 90% or greater.

A "pure stereoisomer," "pure enantiomer," "pure diastereomer," and variants thereof, refer, respectively, to a sample containing a stereoisomer, enantiomer, or diastereomer, which comprises at least about 99.5% of the sample. For pairs of enantiomers and diastereomers, a pure enantiomer or "pure diastereomer" would correspond to samples having an ee or de of about 99% or greater.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Cis" in the context of a pair of monophospholane ring substituents refers to a configuration in which both substituents are located on the same side of the ring. "Trans" in the context of a pair of monophospholane ring substituents refers to a configuration in which the substituents are located on the opposite sides of the ring. The terms "cis/cis," "cis/trans," and "trans/trans" refer to the arrangement of each phospholane ring within one molecule of a bisphospholane.

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Solvate" describes a molecular complex comprising a compound (e.g., pregabalin) and a stoichiometric or non-stoichiometric amount of one or more solvent molecules (e.g., ethanol).

"Hydrate" describes a solvate comprising a compound (e.g., pregabalin) and a stoichiometric or non-stoichiometric amount of water.

"Pharmaceutically acceptable complexes, salts, solvates, or hydrates" refers to complexes, acid or base addition salts, solvates or hydrates of claimed and disclosed compounds, which are within the scope of sound medical judgment, suitable for use in contact with the tissues of patients without undue toxicity, irritation, allergic response, and the like, commensurate with a reasonable benefit/risk ratio, and effective for their intended use.

"Treating" refers to reversing, alleviating, inhibiting the progress of, or preventing a disorder or condition to which such term applies, or to preventing one or more symptoms of such disorder or condition.

"Treatment" refers to the act of "treating" as defined immediately above.

Table 1 provides a non-exhaustive list of abbreviations that may be used in the specification.

TABLE 1

List of Abbreviations

| Abbreviation | Description |
| --- | --- |
| Ac | acetyl |
| ACN | acetonitrile |
| AcNH | acetylamino |
| Aq | aqueous |
| Bn | benzyl |
| bp | boiling point |
| Bu | butyl |
| n-BuLi | normal-butyl lithium |
| Bu$_4$NBr | tetrabutylammonium bromide |
| t-BuNH$_2$ | tertiary-butylamine |
| t-BuOK | potassium tertiary butyl oxide |
| t-BuOMe | tertiary butyl methyl ether |
| t-BuONa | sodium tertiary butyl oxide |
| CBz | benzyloxycarbonyl |
| COD | 1,5-cyclooctadiene |
| DABCO | 1,4-diazabicyclo[2.2.2]octane |
| DBU | 1,8-diazabicyclo[5.4.0]undec-7-ene |
| DEAD | diethylazodicarboxylate |
| DIPEA | diisopropylethylamine (Hünig's Base) |
| DMAP | 4-dimethylaminopyridine |
| DMF | dimethylformamide |
| DMSO | dimethylsulfoxide |
| ee | enantiomeric excess |
| Et | ethyl |
| Et$_3$N | triethylamine |
| Et$_2$NH | diethylamine |
| Et$_2$O | diethylether |
| EtOH | ethyl alcohol |
| EtOAc | ethyl acetate |
| eq | molar equivalents |
| h, min, s | hours, minutes, seconds |
| HOAc | acetic acid |
| IAcOEt | ethyl iodoacetate |
| IPA | isopropanol |
| LiHMDS | lithium hexamethyldisilazide |
| LTMP | lithium tetramethylpiperidide |
| LDA | lithium diisopropylamide |
| Me | methyl |
| MeCl$_2$ | methylene chloride |
| MeI | methyl iodide |
| MeLi | methyl lithium |
| MeONa | sodium methoxide |
| MeOH | methyl alcohol |
| Mpa | mega Pascals |
| Ms | mesyl |
| NMP | N-methylpyrrolidone |
| OTf$^-$ | triflate (trifluoro-methanesulfonic acid anion) |
| Ph | phenyl |
| PhLi | phenyl lithium |
| Ph$_3$P | triphenylphosphine |
| Ph$_3$As | triphenylarsine |
| RI | refractive index |
| RT | room temperature (approximately 20° C.-25° C.) |
| s/c | substrate-to-catalyst molar ratio |
| Tf | trifluoromethanesulfonyl (triflyl) |
| TFA | trifluoroacetic acid |
| THF | tetrahydrofuran |
| TLC | thin-layer chromatography |
| TMEDA | N,N,N',N'-tetramethyl-1,2-ethylenediamine |
| TRITON B | benzyltrimethylammonium hydroxide |
| Ts | tosyl |

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and the like, see T. W. Greene and P. G. Wuts, *Protecting Groups in Organic Chemistry* (1999) and P. Kocienski, *Protective Groups* (2000), which are herein incorporated by reference in their entirety for all purposes.

In addition, some of the schemes and examples below may omit details of common reactions, including oxidations, reductions, and so on, which are known to persons of ordinary skill in the art of organic chemistry. The details of such reactions can be found in a number of treatises, including Richard Larock, *Comprehensive Organic Transformations* (1999); M. B. Smith and J. March, *March's Advanced Organic Chemistry* (5$^{th}$ Ed. 2001); and the multi-volume series edited by Michael B. Smith and others, *Compendium of Organic Synthetic Methods* (1974-2004). Generally, starting materials and reagents may be obtained from commercial sources or derived from literature methods.

The present invention provides materials and methods for preparing P-chirogenic compounds represented by Formula 9 and Formula 10, above. Additionally, the present invention provides materials and methods for preparing P-chirogenic compounds having opposite stereochemical configuration (i.e., opposite enantiomers) of those compounds represented by Formula 9 and Formula 10. Generally, and unless expressly noted or otherwise clear from the context of the text, a reference to a formula showing a compound having a particular stereochemical configuration includes that compound's opposite enantiomer.

Useful compounds of Formula 9 and Formula 10 include monophospholanes and bisphospholanes in which R is $C_{1-6}$ alkyl, halo-$C_{1-6}$ alkyl, $C_{3-8}$ cycloalkyl, halo-$C_{3-8}$ cycloalkyl, $C_{1-6}$ alkoxy, $C_{1-6}$ alkoxy-$C_{1-6}$ alkyl, aryl, or aryl-$C_{1-6}$ alkyl, and X is $C_{1-12}$ alkyl, $C_{1-12}$ alkanediyl, or phen-1,2-diyl, which may be substituted or unsubstituted. Other useful compounds of Formula 9 and Formula 10 include monophospholanes and bisphospholanes in which R is $C_{1-6}$ alkyl, $C_{3-8}$ cycloalkyl, $C_{1-6}$ alkoxy, $C_{1-6}$ alkoxy-$C_{1-6}$ alkyl, aryl, or aryl-$C_{1-4}$ alkyl, and X is $C_{1-6}$ alkyl, $C_{1-6}$ alkanediyl, or phen-1,2-diyl. Particularly useful compounds of Formula 9 and Formula 10 include monophospholanes and bisphospholanes in which R is $C_{1-6}$ alkyl, $C_{1-6}$ alkoxy-$C_{1-6}$ alkyl, or aryl-$C_{1-6}$ alkyl, and X is $C_{1-6}$ alkyl, $C_{1-2}$ alkanediyl, or phen-1,2-diyl. The latter compounds include those in which R is methyl, ethyl, isopropyl, methoxymethyl, or benzyl, and X is methyl, methylene, ethanediyl, or phen-1,2-diyl.

Figure 1:
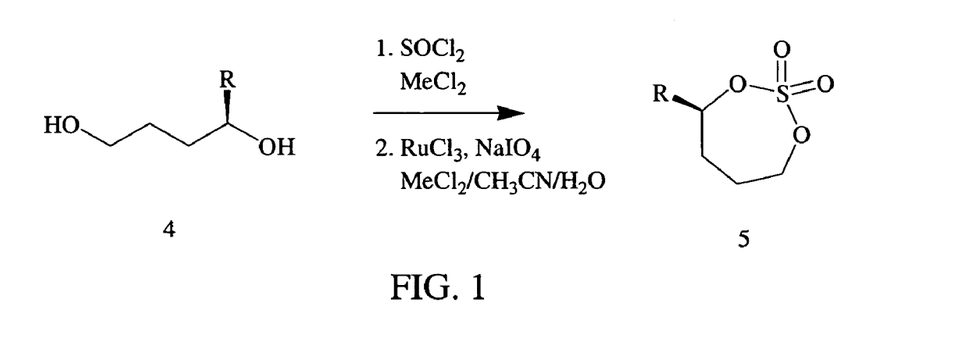
FIG. 1 depicts a scheme for preparing chiral 4-substituted-[1,3,2]dioxathiepane 2,2-dioxides (cyclic sulfates, Formula 5).
Figure 2:
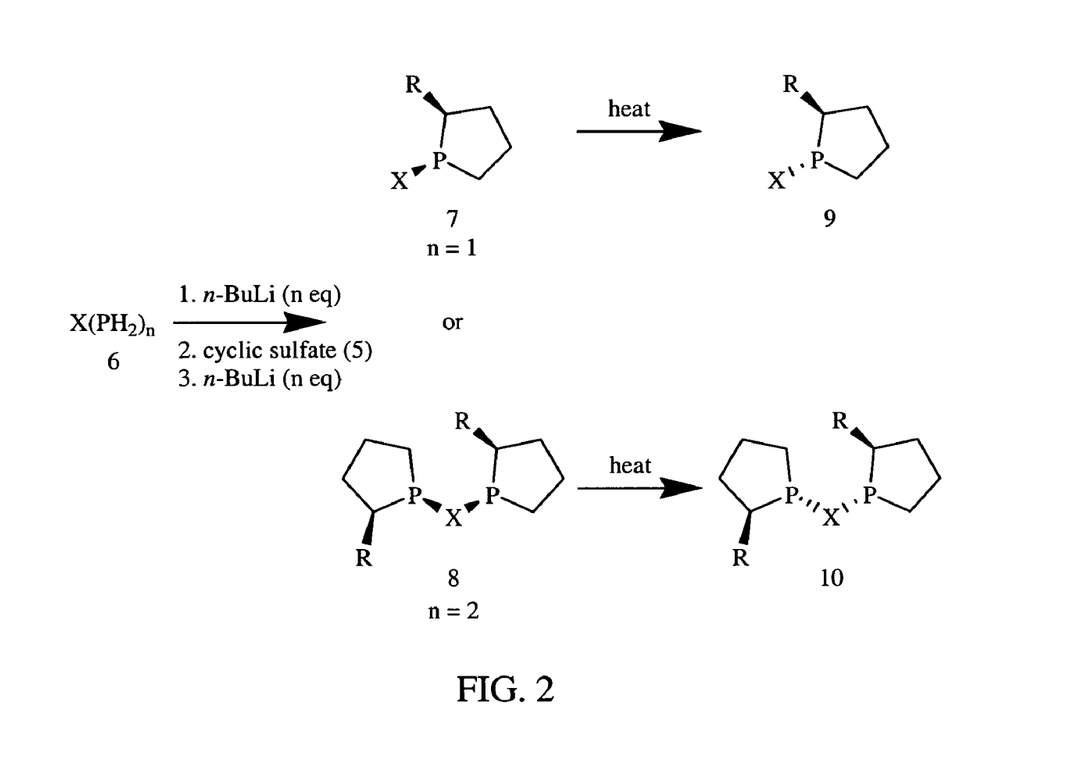
FIG. 2 depicts a scheme for preparing trans monophospholanes (Formula 9) and trans/trans bisphospholanes (Formula 10).

FIG. 1 and FIG. 2 provide schemes for preparing the P-chirogenic monophospholanes and bisphospholanes of Formula 9 and Formula 10. The scheme shown in FIG. 1 illustrates a method of preparing a chiral cyclic sulfate (Formula 5), which is subsequently reacted with a monophosphine or bisphosphine (Formula 6) in the presence of a strong base to give a cis monophospholane (Formula 7) or a cis/cis bisphospholane (Formula 8), respectively. As shown in FIG. 1, a chiral 1,4-diol (Formula 4) is reacted with thionyl chloride to give a corresponding 1,4-diol cyclic sulfite (not isolated), which is subsequently oxidized with NaIO$_4$ and a catalytic amount of RuCl$_3$ to give the cyclic sulfate of Formula 5 as an oil or crystalline solid. The R-substituent in Formula 4 and Formula 5 is as defined above in Formula 9 and Formula 10, and the chiral 1,4-diol of Formula 4 can be obtained from L-glutamic acid and (S)-2,3-epoxypropylbenzene using known methods. See, e.g., G. Hoge, *J. Am. Chem. Soc.* 125:10219 (2003); C. Herdeis, *Synthesis*, 232 (1986); H. Brunner & H. Lautenschlager, *Synthesis*, 706 (1989); K. Mori, *Tetrahedron* 31:3011 (1975); U. Ravid et al., *Tetrahedron* 34:1449 (1978); H. Nemoto et al., *J. Org. Chem.* 50:2764 (1985); X. Cai et al., *Organic Process Research and Development* 3:73 (1999).

As noted above and as shown in the scheme depicted in FIG. 2, the P-chirogenic monophospholanes and bisphospholanes of Formula 9 and Formula 10 are obtained by first reacting a monophosphine (Formula 6, n=1) or bisphosphine (Formula 6, n=2) with a first strong base that is capable of deprotonating a P—H bond, such as MeLi, n-BuLi, PhLi, or LDA. The resulting anion is reacted with the chiral cyclic sulfate (Formula 5) to produce a carbon-phosphorus bond on each phosphorus atom. Subsequent treatment with a second strong base (which may be the same as or different than the first strong base) removes the remaining proton on each of the phosphorus atoms, which results in a second carbon-phosphorus bond and generates, via sulfate group displacement, a cis monophospholane (Formula 7) or a cis/cis bisphospholane (Formula 8). The reaction may be carried out in an organic solvent, such as THF, Et$_2$O, dimethoxyethane, and the like, under an inert atmosphere (e.g., nitrogen or argon) and at a temperature between about 0° C. and reflux conditions. The cyclization is generally carried out at ambient pressure.

The cyclizations depicted in FIG. 2 generally provide good cis-to-trans ratios of monophospholanes (Formula 7) and cis/cis-to-cis/trans ratios of the bisphospholanes (Formula 8). As described in the Examples section, in many cases, the cis and cis/cis diastereoisomers may be isolated from mixtures of cis and trans isomers and from mixtures of cis/cis and cis/trans isomers via crystallization or column chromatography of borane or sulfide adducts of the phosphines. As also described in Examples section, the method shown in FIG. 2 does not appear to generate trans/trans isomers.

The cis and cis/cis stereochemistry observed for the monophospholanes (Formula 7) and bisphospholanes (Formula 8) is surprising. Although researchers have recently reported cis stereoselectivity in a cyclization, the elucidation of the mechanism of stereoselectivity in those studies was complicated by the existence of many chiral substituents in the cyclization precursor. See E. Vedejs & O. Daugulis, *J. Am. Chem. Soc.* 121:5813 (1999); E. Vedejs, O. Daugulis, *J. Am. Chem. Soc.* 125:4166 (2003).

Figure 3:
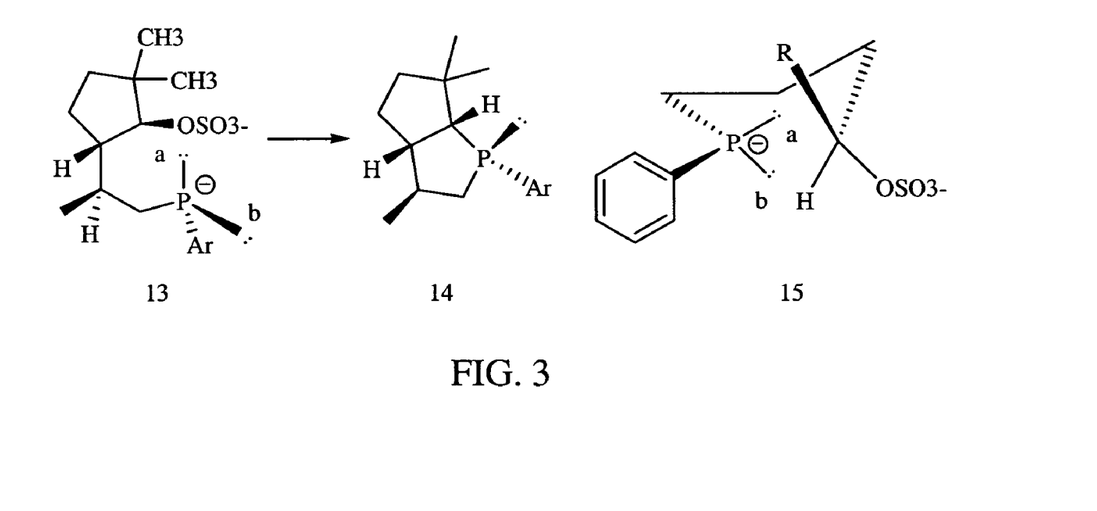
FIG. 3 compares a stereoselective cyclization mechanism of Vedejs & Daugulis with a proposed stereoselective cyclization mechanism for the phospholane formation shown in FIG. 2.

FIG. 3 compares the stereoselective cyclization mechanism of Vedejs & Daugulis (Formula 13 and Formula 14) with a proposed stereoselective cyclization mechanism for the phospholane formation shown in FIG. 2. Vedejs & Daugulis credited 1,3 interactions for the observation that lone pair "a" in Formula 13 was favored for displacement of the sulfate group. The resulting product Formula 14) is analogous to the cis monophospholanes (Formula 7) and cis/cis bisphospholanes (Formula 8) depicted in FIG. 2 since the Ar (aryl) group on the phosphorous atom in Formula 14 is cis with respect to the fused 5-membered carbocyclic ring. By analogy, an intermediate in our system is presumably represented by Formula 15. Given the lack of 1,3 interactions in Formula 15, the lowest energy approach of lone pair "a" to displace the sulfate group is attributed to phenyl substituent steric interaction with an unknown lowest energy transition state phospholane ring structure.

As shown in FIG. 2, the trans monophospholanes (Formula 9) and trans/trans bisphospholanes (Formula 10) are prepared from the corresponding cis monophospholanes (Formula 7) and bisphospholanes (Formula 8) via epimerization. Pyramidal inversion is a well-known phenomenon for phosphines, as well as for other atoms. See, e.g., H. Hommer & B. Gordillo, *Phosphorous, Sulfur, and Silicon* 177:465 (2002); W. Egan et al., *J. Am. Chem. Soc.* 92:1442 (1970); S. E. Cremer et al., Tetrahedron Lett. 55:5799 (1968). See also, J. B. Lambert, Topics in Stereochemistry, 6:19 (1971); A. Rauk et al., Angew. Chem. International Edition 9:400 (1970). However, this subtle transformation has been underutilized in practical synthesis of P-chirogenic phosphines. Epimerization via pyramidal inversion represents an ideal reaction in terms of atom efficiency and work-up.

As shown in FIG. 2, the cis monophospholanes (Formula 7) and bisphospholanes (Formula 8) may be epimerized to the trans monophospholanes (Formula 9) and trans/trans bisphospholanes (Formula 10), respectively, by heating the compounds of Formula 7 or Formula 8 to a temperature below the decomposition temperature of the reactants and products. For reasonable reaction times, the epimerization substrate is heated to a temperature between about 100° C. and 250° C., inclusive. Reagents and solvent are not necessary to promote epimerization. Though not necessary, the epimerization may be carried out in the absence of oxygen to minimize oxide formation. Generally, maintaining the oxygen content in the headspace above the reaction mixture to less than about 1% based on mass is sufficient. As shown in the Examples, epimerization yields may approach 100%.

When epimerized products (Formula 8 and Formula 9) are desired, it is convenient to cyclize and then epimerize via a one-pot procedure. Solvent from cyclization reactions may be removed invacuo and the resulting residue (a mixture of predominantly cis or cis/cis phospholanes and sulfate salts) is heated to the appropriate temperature without solvent in an oil bath under a nitrogen atmosphere.

Figure 4:
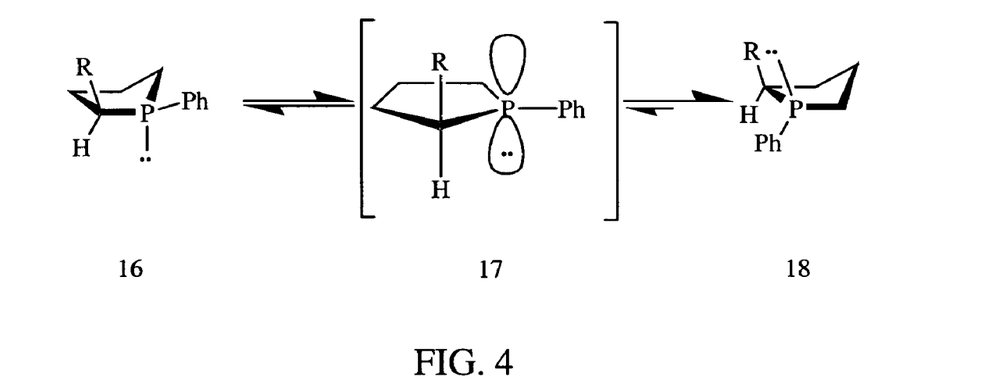
FIG. 4 depicts a pyramidal inversion mechanism for epimerizing cis monophospholanes (Formula 7) to trans monophospholanes (Formula 9).

Although not bound to any particularly theory, the epimerization mechanism may be explained using a monophospholane (Formula 16) shown in FIG. 4. The mechanism likely involves a transition state featuring an $sp^2$ phosphorous atom (Formula 17) that is in equilibrium with each form of the phospholane (Formula 16 and Formula 18). The reaction is driven toward the more thermodynamically stable trans phospholane (Formula 18). As noted in the Examples, certain bisphospholanes (Formula 8, R=Me, X=phen-1,2-diyl, and R=Bn, X=ethanediyl) and monophospholanes (Formula 7, R=Me, X=phenyl) undergo incomplete epimerization. This is probably the result of similar energies of cis versus trans isomers due to lessened steric effects of the small methyl substituents. In addition, the benzyl-substituted bisphospholane (Formula 8, R=Bn, X=ethanediyl) is probably difficult to epimerize because the $sp^2$ phosphorous atom in the transition state is not stabilized by an aryl group bridging the two phospholane groups.

Figure 5:
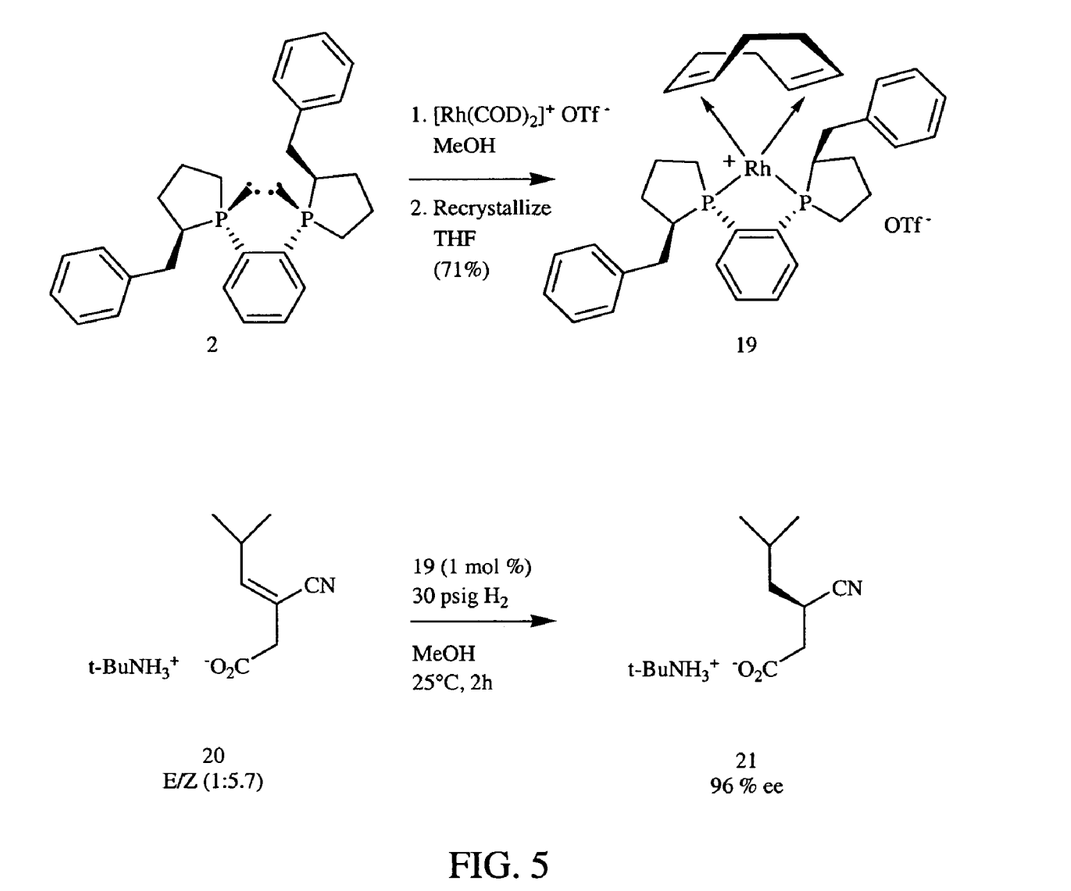
FIG. 5 depicts a scheme for preparing a chiral precursor (Formula 21) of pregabalin using a chiral catalyst (Formula 19) comprised of a P-chirogenic bisphospholane ligand (Formula 2) and rhodium.

FIG. 5 shows a scheme for preparing a chiral precursor (Formula 21) of pregabalin using a chiral catalyst (Formula 19) comprised of a P-chirogenic bisphospholane ligand (Formula 2) and rhodium. As shown in FIG. 5, the bisphospholane ligand was converted to a cationic rhodium complex (Formula 19) via reaction with $[Rh(COD)^2]^+$ OTf$^-$ in MeOH. The rhodium complex was subsequently used to catalyze the asymmetric hydrogenation of a cyano-substituted prochiral olefin (Formula 20) to give the chiral precursor (Formula 21), which was the sole hydrogenation product (96% ee).

Generally, the chemical transformations described throughout the specification may be carried out using substantially stoichiometric amounts of reactants, though certain reactions may benefit from using an excess of one or more of the reactants. Additionally, many of the reactions disclosed throughout the specification, may be carried out at about RT, but particular reactions may require the use of higher or lower temperatures, depending on reaction kinetics, yields, and the like. In addition, any reference in the disclosure to a stoichiometric range, a temperature range, a pH range, etc., includes the indicated endpoints.

Desired enantiomers of any of the compounds disclosed herein may be further enriched through classical resolution, chiral chromatography, or recrystallization. For example, compounds having stereogenic centers may be reacted with an enantiomerically-pure compound (e.g., acid or base) to yield a pair of diastereoisomers, each composed of a single enantiomer, which are separated via, say, fractional recrystallization or chromatography. The desired enantiomer is subsequently regenerated from the appropriate diastereoisomer. Additionally, the desired enantiomer often may be further enriched by recrystallization in a suitable solvent when it is it available in sufficient quantity (e.g., typically not much less than about 85% ee, and in some cases, not much less than about 90% ee).

Many of the compounds described in this disclosure are capable of forming pharmaceutically acceptable salts. These salts include, without limitation, acid addition salts (including diacids) and base salts. Pharmaceutically acceptable acid addition salts include nontoxic salts derived from inorganic acids such as hydrochloric, nitric, phosphoric, sulfuric, hydrobromic, hydroiodic, hydrofluoric, phosphorous, and the like, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like.

Pharmaceutically acceptable base salts include nontoxic salts derived from bases, including metal cations, such as an alkali or alkaline earth metal cation, as well as amines. Examples of suitable metal cations include, without limitation, sodium cations ($Na^+$), potassium cations ($K^+$), magnesium cations ($Mg^{2+}$), calcium cations ($Ca^{2+}$), and the like. Examples of suitable amines include, without limitation, N,N'-dibenzylethylenediamine, chloroprocaine, choline, diethanolamine, dicyclohexylamine, ethylenediamine, N-methylglucamine, and procaine. For a discussion of useful acid addition and base salts, see S. M. Berge et al., "Pharmaceutical Salts," 66 *J. of Pharm. Sci.*, 1-19 (1977); see also Stahl and Wermuth, *Handbook of Pharmaceutical Salts: Properties, Selection, and Use* (2002).

One may prepare a pharmaceutically acceptable acid addition salt (or base salt) by contacting a compound's free base (or free acid) with a sufficient amount of a desired acid (or base) to produce a nontoxic salt. One may then isolate the salt by filtration if it precipitates from solution, or by evaporation to recover the salt. One may also regenerate the free base (or free acid) by contacting the acid addition salt with a base (or the base salt with an acid). Though certain physical properties of the free base (or free acid) and its respective acid addition salt (or base salt) may differ (e.g., solubility, crystal structure, hygroscopicity, etc.), a compound's free base and acid addition salt (or its free acid and base salt) are otherwise the same for purposes of this disclosure.

Additionally, certain compounds of this disclosure may exist as an unsolvated form or as a solvated form, including hydrated forms. Pharmaceutically acceptable solvates include hydrates and solvates in which the crystallization solvent may be isotopically substituted, e.g. $D_2O$, $d_6$-acetone, $d_6$-DMSO, etc. Generally, for the purposes of this disclosure, solvated forms, including hydrated forms, are the same as unsolvated forms. Thus, unless expressly noted, all references to the free base, the free acid or the unsolvated form of a compound also includes the corresponding acid addition salt, base salt or solvated form of the compound.

The disclosed compounds also include all pharmaceutically acceptable isotopic variations, in which at least one atom is replaced by an atom having the same atomic number, but an atomic mass different from the atomic mass usually found in nature. Examples of isotopes suitable for inclusion in the disclosed compounds include, without limitation, isotopes of hydrogen, such as $^2H$ and $^3H$; isotopes of carbon, such as $^{13}C$ and $^{14}C$; isotopes of nitrogen, such as $^{15}N$; isotopes of oxygen, such as $^{17}O$ and $^{18}O$; isotopes of phosphorus, such as $^{31}P$ and $^{32}P$; isotopes of sulfur, such as $^{35}S$; isotopes of fluorine, such as $^{18}F$; and isotopes of chlorine, such as $^{36}Cl$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies.

EXAMPLES

The following examples are intended to be illustrative and non-limiting, and represent specific embodiments of the present invention.

General Methods and Materials

All reactions and manipulations were performed under nitrogen in standard laboratory glassware. Rhodium complex recrystallization and asymmetric hydrogenation were performed in a nitrogen filled glovebox. THF (anhydrous, 99.9%), acetonitrile (anhydrous, 99.8%), ether (anhydrous, 99.8%), methyl alcohol (anhydrous, 99.8%), and dichloromethane (anhydrous, 99.8%) were obtained from Aldrich Chemical Co. Thionyl chloride (99.5%), ruthenium (III) chloride hydrate (99.98%), sodium periodate (99%), and n-BuLi (2.5 M in hexanes) were obtained from Aldrich Chemical Co. Bis(1,5-cyclooctadiene)rhodium (I) trifluoromethanesulfonate (99%), 1,2-bis(phosphino)benzene (98+%), 1,2-bis(phosphino)ethane (99%), and phenylphosphine (99%) were obtained from Strem Chemicals, Inc. Hydrogen gas was used from a lecture bottle supplied by Specialty Gas. Hydrogenations were performed in a Griffin-Worden pressure vessel supplied by Kimble/Kontes.

Example 1

Preparation of (4S)-4-Benzyl-1,3,2-dioxathiepane 2,2-dioxide (Formula 5, R=Bn)

To a 250 mL round bottom flask was dissolved (S)-5-phenyl-pentane-1,4-diol (Formula 4, R=Bn, 8.97 g, 49.8 mmol) in $CH_2Cl_2$ (150 mL) and then placed under $N_2$ and cooled to 0° C. Thionyl chloride (4.54 mL, 62.2 mmol) was added in one portion via a syringe. No exotherm was observed. The reaction was warmed to room temperature and stirred for 30 minutes. Gaseous HCl was observed evolving from the solution. The solution was light brown. The reaction was then placed in an oil bath and refluxed open to air for 15 hours. The $CH_2Cl_2$ was then removed on a rotary evaporator. The light brown residue was redissolved in $CH_2Cl_2$ (150 mL) and $CH_3CN$ (150 mL). To this solution was added $H_2O$ (300 mL). The resulting solution was cooled to 0° C. and stirred in air. $RuCl_3.xH_2O$ (0.112 g, 0.498 mmol) was added in one portion and then sodium periodate (21.3 g, 99.5 mmol) was added portionwise until it became apparent that the reaction would not exotherm. The reaction was stirred for 5 hours during which it turned from light brown to black. The reaction was transferred to a separatory funnel and the black bottom layer was separated. The top aqueous layer was then extracted with ethyl ether (300 mL). The ether layer was combined with the black bottom layer and the resulting solution was filtered through a short plug of silica gel washing with ethyl ether to produce a light yellow solution. The filtration was needed to remove Ru salts. Volatiles were removed on a rotary evaporator leaving a light green oil. The oil recrystallized upon standing for 20 minutes. A small amount of ethyl ether was added and then the crystals were collected and washed with hexane producing a white crystalline product (4.83 g). A second crop formed in the mother liquor after addition of hexane (from the washes) yielding additional white crystals (3.30 g). The white crystalline product was stable in air for greater than 6 months. Any ruthenium salts remaining in the crystalline product (as observed by the appearance of green solids after redissolving the crystals in THF) may be removed by redissolving the product in THF, filtering the suspension through a short plug of silica gel, and recrystallizing the filtrate. Yield: 67%; $[\alpha]^{24}_D$=+16.0° (c 1.0, CHCl3); $^1H$ NMR (400 MHz, $CDCl_3$) δ 1.97 (m, 4 H) 2.92 (dd, J=13.91, 7.08 Hz, 1 H) 3.14 (dd, J=14.03, 6.22 Hz, 1 H) 4.34 (m, J=12.08, 3.42, 3.29 Hz, 1 H) 4.45 (m, J=11.83, 11.83, 1.46 Hz, 1 H) 4.83 (m, 1 H) 7.22 (m, 2 H) 7.29 (m, 3 H); $^{13}C$ NMR (101 MHz, $CDCl_3$) δ 27.41, 32.02, 41.79, 71.91, 85.19, 127.45, 128.95, 129.73, 135.57. Anal. Calc'd for $C_{11}H_{14}O_4S$: C, 54.53; H, 5.82. Found: C, 54.60; H, 5.77.

Example 2

Preparation of (4R)-4-Methyl-1,3,2-dioxathiepane 2,2-dioxide (Formula 5, R=Me)

The titled compound was prepared from (R)-pentane-1,4-diol and $SOCl_2$ using a method similar to the procedure in Example 1. The resulting oil was chromatographed over silica gel (25% ethyl acetate/hexanes) to provide the titled compound. Yield: 48%; normal bp 117.2° C.; $[\alpha]^{24}_D$=−6.1° (c 1.0, $CHCl_3$); $^1H$ NMR (400 MHz, $CDCl_3$) δ 1.43 (d, J=6.34 Hz, 3 H) 1.94 (m, 3 H) 2.11 (m, 1 H) 4.35 (m, 1H) 4.44 (td, J=11.90, 1.34 Hz, 1 H) 4.79 (m, J=15.10, 6.30, 6.30, 3.05 Hz, 1 H); $^{13}C$ NMR (101 MHz, $CDCl_3$) δ 21.65, 27.42, 34.68, 72.01, 82.06; HRMS (EI): $(M+H)^+$167.0337 ($(M+H)^+$, exact mass calc'd for $C_5H_{11}O_4S$: 167.0378).

Example 3

Preparation of (4S)-4-(Methoxymethyl)-1,3,2-dioxathiepane 2,2-dioxide (Formula 5, R=methoxymethyl)

The titled compound was prepared from (S)-5-methoxy-pentane-1,4-diol and $SOCl_2$ using a method similar to the procedure in Example 1. The resulting oil was chromatographed over silica gel (25% ethyl acetate/hexanes) to provide the titled compound. Yield: 53% yield; $[\alpha]^{24}_D$=−9.8° (c 1.0, $CHCl_3$); 1H NMR (400 MHz, $CDCl_3$) δ ppm 2.00 (m, 3 H) 2.10 (m, 1 H) 3.39 (d, J=2.68 Hz, 3 H) 3.50 (dd, J=10.86, 4.76 Hz, 1 H) 3.59 (dd, J=10.74, 5.37 Hz, 1 H) 4.38 (m, 1 H)

4.46 (td, J=11.71, 1.46 Hz, 1 H) 4.71 (m, 1 H); $^{13}$C NMR (101 MHz, CDCl$_3$) δ ppm 27.14, 29.50, 59.61, 72.12, 73.65, 82.61. Anal. calc'd for C$_6$H$_{12}$O$_5$S: C, 36.73; H, 6.16. Found: C, 36.74; H, 6.01.

Example 4

Preparation of (1R,2R)-1-Phenyl-2-benzylpholane (Formula 7, R=Bn, X=Ph)

To a 25 mL round bottom flask equipped with a magnetic stirring bar was added phenylphosphine (0.300 g, 2.73 mmol). To the flask was added THF (10 mL) via a syringe and the reaction mixture was placed under nitrogen and cooled to 0° C. To the solution was added n-BuLi (1.0 eq, 1.0 mL of a 2.5M solution in hexanes) and the reaction mixture was stirred for 1 hour at 0° C. The reaction solution was yellow, which was indicative of phosphine anion formation. A solution of (4S)-4-benzyl-1,3,2-dioxathiepane 2,2-dioxide in THF (5 mL) was then added via a syringe. The reaction was stirred for 30 minutes at 0° C. and then for 30 minutes at room temperature. The reaction was cooled back down to 0° C. and then n-BuLi (1.15 eq, 1.25 mL of a 2.5M solution in hexanes) was added dropwise over five minutes. The reaction was stirred for 30 minutes at 0° C. and then warmed to room temperature and stirred for 45 minutes. The reaction was quenched with MeOH (1 mL) to produce a white chunky solution. The volatiles were removed invacuo and then the white oily solid was triturated with ethyl ether and then filtered to remove the sulfate salts. The solvent in the filtrate was then removed invacuo to give a clear oil (603 mg). Yield: 82%; cis:tran=9.4:1; $^{31}$P NMR (162 MHz, CDCl$_3$) δ ppm −7.0 (s).

Example 5

Preparation of (1R,2R)-1-Phenyl-2-benzylpholaneborane (Formula 22)

22

(1R,2R)-1-Phenyl-2-benzylpholane (Example 4) was converted to its phosphine borane derivative, (1R,2R)-1-phenyl-2-benzylpholaneborane, for characterization purposes. The phospholane was dissolved in THF (10 mL) under nitrogen and stirred with a magnetic stir bar. To this solution was added BH$_3$.Me$_2$S (0.273 mL of a 10.0 M solution) via a syringe. The reaction was stirred for 30 minutes and then the volatiles were removed on a rotary evaporator to produce a white solid. The white solid was recrystallized from hot ethyl acetate (15% in hexanes) to produce white crystals (440 mg). Yield: 61% from (4S)-4-benzyl-1,3,2-dioxathiepane 2,2-dioxide; [α]$^{20}$$_D$=−1.3° (c 1.0, CHCl$_3$); $^1$H NMR (400 MHz, CDCl$_3$) δ 0.86 (m, 3 H) 1.55 (m, 1 H), 1.79 (m, 1 H), 2.04 (m, 2 H), 2.24 (m, 3H), 2.40 (m, 1H), 2.67 (m, 1 H), 6.98 (m, 2 H), 7.18 (m, 3 H), 7.51 (m, 3 H), 7.73 (m, 2 H); $^{13}$C NMR (101 MHz, CDCl$_3$) δ 25.13, 25.46 (d, J=36.85 Hz), 33.73, 35.82, 42.24, 126.54, 127.74 (d, J=43.76 Hz), 128.67 (d, J=18.43 Hz), 128.92 (d, J=9.21 Hz), 128.96, 131.75 (d, J=2.30 Hz), 133.25 (d, J=8.45 Hz), 140.04 (d, J=10.75 Hz); $^{31}$P NMR (162 MHz, CDCl$_3$) δ 32.76. Anal. calc'd for C$_{17}$H$_{22}$BP: C, 76.15; H, 8.27. Found: C, 73.16; H, 8.29.

Example 6

Preparation of (1R,2S)-1-Phenyl-2-methylphospholane (Formula 7, R=Me, X=Ph)

The titled compound was prepared from (4R)-4-methyl-1,3,2-dioxathiepane 2,2-dioxide and phenylphosphine using a method similar to the procedure in Example 4. Yield: 72%; cis:trans=7.0:1; $^{31}$P NMR (162 MHz, CDCl$_3$) δ ppm −5.80 (s).

Example 7

(1R,2S)-1-Phenyl-2-methylphospholaneborane (Formula 23)

23

(1R,2S)-1-Phenyl-2-methylphospholane (Example 6) was converted to its phosphine borane derivative, (1R,2S)-1-phenyl-2-methylphospholaneborane, for characterization purposes, by reaction with BH$_3$.Me$_2$S in a manner similar to the procedure in Example 5. The resulting diastereoisomers were isolated as an oil, but were inseparable via column chromatography over silica gel. $^1$H NMR (400 MHz, CDCl$_3$) δ 0.84 (m, 3 H) 0.83 (dd, J=14.41, 6.59 Hz, 3 H) 1.53 (m, 1 H) 1.85 (m, 1 H) 2.19 (m, 5 H) 7.48 (m, 3 H) 7.68 (m, 2 H); $^{13}$C NMR (101 MHz, CDCl$_3$) δ 14.06, 25.09 (d, J=36.08 Hz), 34.64, 35.07 (d, J=36.08 Hz), 36.10, 128.79 (m, J=9.21 Hz), 131.48, 133.09 (d, J=8.44 Hz); 31P NMR (162 MHz, CDCl$_3$) δ 33.84 (m). HRMS (EI): (M−BH$_3$+H)$^+$179.1136 ((M−BH$_3$+H)$^+$, exact mass calc'd for C$_{11}$H$_{16}$P: 179.0990).

Example 8

Preparation of (1R,2R)-1-Phenyl-2-(methoxymethyl)phospholane (Formula 7, R=methoxymethyl, X=Ph)

The titled compound was prepared from (4S)-4-(methoxymethyl)-1,3,2-dioxathiepane 2,2-dioxide and phenylphosphine using a method similar to the procedure in Example 4. Yield: 70%; cis:trans=16.5:1; $^{31}$P NMR (162 MHz, CDCl$_3$) δ ppm −10.7 (s).

Example 9

Preparation of (1R,2R)-1-Phenyl-2-(methoxymethyl)phospholane-sulfide (Formula 24)

24

(1R,2R)-1-Phenyl-2-(methoxymethyl)phospholane was converted to its phosphine sulfide derivative, (1R,2R)-1-phenyl-2-(methoxymethyl)phospholane-sulfide, for characterization purposes. The crude phospholane from the cyclization procedure was dissolved in toluene and then sulfur (1.25 eq based on (4S)-4-(methoxymethyl)-1,3,2-dioxathiepane 2,2-dioxide) was added in one portion. The reaction was warmed to 50° C. and stirred under nitrogen for 12 hours and then the volatiles were removed invacuo producing a clear oil. The oil was chromatographed over silica gel (30% ethyl acetate in hexanes) producing the titled compound as a single diastereomer. Yield: 31% from (4S)-4-(methoxymethyl)-1,3,2-dioxathiepane 2,2-dioxide; bp 171.3° C.; $[\alpha]^{24}_D$=+56.20 (c 1.0, $CHCl_3$); 1H NMR (400 MHz, $CDCl_3$) δ 1.60 (m, 1 H) 2.23 (m, 4 H) 2.63 (m, 2 H) 2.97 (m, 1 H) 2.97 (s, 3 H) 3.12 (m, 1 H) 7.48 (m, 3 H) 7.86 (m, 2 H); 13C NMR (101 MHz, $CDCl_3$) δ ppm 24.32 (d, J=4.61 Hz), 30.99 (d, J=9.21 Hz), 34.16 (d, J=54.51 Hz), 50.00 (d, J=52.21 Hz), 58.66, 71.25 (d, J=3.07 Hz), 128.52 (d, J=11.52 Hz), 128.88 (d, J=11.52 Hz), 130.27 (d, J=67.56 Hz), 131.82 (d, J=9.98 Hz); $^{31}$P NMR (162 MHz, $CDCl_3$) δ ppm 60.72 (s). Anal. calc'd for $C_{12}H_{20}BOP$: C, 59.98; H, 7.13. Found: C, 59.95; H, 7.07.

Example 10

Preparation of 1,2-Bis((1R,2R)-2-benzylphospholano)benzene (Formula 8, R=Bn, X=phen-1,2-diyl)

To a 25 mL round bottom flask equipped with a magnetic stirring bar was added 1,2-Bis(phosphino)benzene (0.330 g, 2.33 mmol). To the flask was added THF (15 mL) via a syringe and the reaction was placed under nitrogen and cooled to 0° C. To the solution was added n-BuLi (1.0 eq, 1.9 mL of a 2.5M solution in hexanes) and the reaction was stirred for 1 hour at 0° C. The reaction solution was yellow, which was indicative of phosphine anion formation. A solution of (4S)-4-benzyl-1,3,2-dioxathiepane 2,2-dioxide in THF (5 mL) was then added via a syringe. The reaction mixture was stirred for 30 minutes at 0° C. and then for 30 minutes at room temperature. The reaction was cooled back down to 0° C. and then n-BuLi (2.3 eq, 2.1 mL of a 2.5M solution in hexanes) was added dropwise over five minutes. The reaction was stirred for 30 minutes at 0° C. and then warmed to room temperature and stirred for 45 minutes. The reaction was quenched with MeOH (1 mL) to produce a white chunky solution. The volatiles were removed invacuo and then the white oily solid was triturated with ethyl ether and then filtered to remove the sulfate salts. The solvent in the filtrate was then removed invacuo producing the titled compound as a clear oil (780 mg). Yield: 78%; cis/cis:cis/trans=4.2:1. The product may be recrystallized from hot 10:1 $MeOH/CHCl_3$ to produce the pure cis/cis diastereomer (60% recovery). $^1$H NMR (400 MHz, $CDCl_3$) δ 1.40 (m, 2 H), 1.61 (m, 4 H), 1.80 (dd, J=13.68, 11.72 Hz, 2 H), 2.00 (m, 6 H), 2.46 (m, 2 H), 3.00 (dd, J=13.68, 3.66 Hz, 2H), 6.97 (m, 4H), 7.06 (m, 2H), 7.14 (m, 4H), 7.29 (m, 2H), 7.37 (m, 2H) $^{13}$C NMR (101 MHz, CDCl3) δ 24.07, 26.09, 32.70, 38.59 (t, J=3.84 Hz), 42.62 (t, J=7.68 Hz), 128.32 (m, J=5.37 Hz), 128.45, 128.92, 131.64 (t, J=1.54 Hz), 142.59 (t, J=3.84 Hz), 143.99; $^{31}$P NMR (162 MHz, $CDCl_3$) δ-16.53 (s).

Example 11

Preparation of 1,2-Bis((1R,2S)-2-methylphospholano)benzene (Formula 8, R=Me, X=phen-1,2-diyl)

The titled compound was prepared from (4R)-4-methyl-1,3,2-dioxathiepane 2,2-dioxide and 1,2-bis(phosphino)benzene using a method similar to the procedure in Example 10. Yield: 52%; cis/cis:cis/tran=6.1:1; $^{31}$P NMR (162 MHz, $CDCl_3$) δ ppm −15.1 (s).

Example 12

Preparation of 1,2-Bis((1R,2S)-2-methylphospholanosulfide)-benzene (Formula 25)

25

1,2-Bis((1R,2S)-2-methylphospholano)benzene was converted to its phosphine sulfide derivative, 1,2-bis((1R,2S)-2-methylphospholanosulfide)benzene, for characterization purposes, by reaction with sulfur (2.2 eq) in a manner similar to the procedure in Example 9. The resulting white solid was recrystallized from hot toluene producing the titled compound as a single diastereomer. Yield: 44% from (4R)-4-methyl-1,3,2-dioxathiepane 2,2-dioxide; $[\alpha]^{24}_D$=+2.30°(c 1.0, $CHCl_3$); $^1$H NMR (400 MHz, $CDCl_3$) δ 0.98 (dd, J=19.29, 7.57 Hz, 6 H), 1.76 (m, 2 H), 1.96 (m, 2H), 2.25 (m, 4H), 2.45 (m, 2H), 3.14 (s, 4H), 7.50 (m, 2H), 7.64 (m, 2H); $^{13}$C NMR (101 MHz, $CDCl_3$) δ 18.47, 23.30 (t, J=3.84 Hz), 33.16, 42.60 (d, J=52.98 Hz), 130.50, 132.99 (t, J=9.21 Hz), 135.93 (dd, J=66.03, 6.91 Hz); $^{31}$P NMR (162 MHz, $CDCl_3$) δ 71.84 (s); HRMS (EI): (M+H)+343.0887 ((M+H)$^+$, exact mass calc'd for $C_{16}H_{25}P_2S_2$: 343.0873).

Example 13

Preparation of 1,2-Bis((1S,2R)-2-benzylphospholano)ethane (Formula 8, R=Bn, X=ethandiyl)

The titled compound was prepared from (4S)-4-benzyl-1,3,2-dioxathiepane 2,2-dioxide and 1,2-bis-phosphanylethane using a method similar to the procedure in Example 10. Yield: 49%; cis/cis:cis/trans=6.1:1; $^{31}$P NMR (162 MHz, $CDCl_3$) δ −13.3 (s).

Example 14

Preparation of 1,2-Bis((1S,2R)-2-benzylphospholaneborane)-ethane (Formula 26)

26

1,2-Bis((1S,2R)-2-benzylphospholano)ethane was converted to its bis-borane derivative, 1,2-bis((1S,2R)-2-benzylphospholaneborane)ethane, for characterization purposes, by reaction with $BH_3.Me_2S$ (2 eq) in a manner similar to the procedure in Example 5. Recrystallization of the product from isopropanol provided the titled compound as a single diastereomer. Yield: 35%; $[\alpha]^{24}_D=-25.30$ (c 1.0, CHCl3); 1H NMR (400 MHz, CDCl$_3$) δ 0.69 (m, 6H), 1.42 (m, 2H), 1.68 (m, H), 2.01 (m, 8H), 2.33 (m, 2H), 2.52 (m, 2H), 3.00 (m, 2H), 7.21 (m, 10H); $^{13}$C NMR (101 MHz, CDCl$_3$) δ 16.46 (d, J=25.34 Hz), 24.64, 24.96 (d, J=34.55 Hz), 33.05, 34.70, 40.48 (d, J=33.01 Hz), 126.85, 128.79, 128.83, 139.51 (d, J=9.98 Hz); $^{31}$P NMR (162 MHz, CDCl$_3$) δ 36.78 (s). Anal. calc'd for C$_{24}$H$_{38}$B$_2$P$_2$: C, 70.29; H 9.34. Found: C, 70.15; H, 9.45.

Example 15 to 20

Preparation of Trans Monophospholanes (Formula 9) and Trans/Trans Bisphospholanes (Formula 10)

One-Pot Sequential Cyclization and Epimerization. After quenching the cyclization reaction in Example 4, 6, 8, 10, 11, and 13 with MeOH and removing the solvent, each of the crude cis monophospholanes (Formula 7) and cis/cis bisphospholanes (Formula 8) was placed under N$_2$ and heated in an oil bath to 190° C. for 8 hours (cyclization products of Example 4, 6, 8, 10, and 11) or 205° C. for 20 hours (cyclization products of Example 13). After cooling to room temperature, the vacuum attachment was quickly replaced with a septum and the flask immediately placed under N$_2$. Care was taken to cool the epimerization product before exposing to air for a short time to avoid oxidation. To the flask was added ethyl ether (15 mL) via a syringe and the product, which had a jelly consistency, was vigorously triturated. The ethyl ether was collected using a syringe equipped with a six-inch needle and filtered through a 0.20 micron SFCA syringe filter into another round bottom under N$_2$. White solid remained in the flask (sulfate salts). The trituration was repeated twice. Combining the ether extractions and evaporating the solvent using a vacuum pump yielded an oil product. $^{31}$P NMR of an aliquot of the oil showed clean conversion to predominantly trans and trans/trans products in ratios described below.

Example 15

(1S,2S)-1-Phenyl-2-methylphospholane (Formula 9, R=Me, X=Ph)

The titled compound was prepared by epimerizing (1R,2S)-1-phenyl-2-methylphospholane (Formula 7, R=Me, X=Ph). Cis:trans=1:3.2; $^{31}$P NMR (162 MHz, CDCl$_3$) δ 2.2 (s).

Example 16

(1S,2R)-1-Phenyl-2-(methoxymethyl)phospholane (Formula 9, R=methoxymethyl, X=Ph)

The titled compound was prepared by epimerizing (1R,2R)-1-phenyl-2-(methoxymethyl)phospholane (Formula 7, R=methoxymethyl, X=Ph). Cis:trans=1:7.1; $^{31}$P NMR (162 MHz, CDCl$_3$) δ −6.2 (s).

Example 17

(1S,2R)-1-Phenyl-2-benzylphospholane (Formula 9, R=Bn, X=Ph)

The titled compound was prepared by epimerizing (1R,2R)-1-phenyl-2-benzylphospholane (Formula 7, R=Bn, X=Ph). Trans 100%; $^{31}$P NMR (162 MHz, CDCl$_3$) δ −2.9 (s).

Example 18

Preparation of 1,2-Bis((1S,2S)-2-methylphospholano)benzene (Formula 10, R=Me, X=phen-1,2-diyl)

The titled compound was prepared by epimerizing 1,2-bis((1R,2S)-2-methylphospholano)benzene (Formula 8, R=Me, X=phen-1,2-diyl). Cis/trans:trans/trans=1:4; $^{31}$P NMR (162 MHz, CDCl$_3$) δ 6.2 (s).

Example 19

Preparation of 1,2-Bis((1S,2R)-2-benzylphospholano)benzene (Formula 8, R=Bn, X=phen-1,2-diyl)

The titled compound was prepared by epimerizing 1,2-bis((1R,2R)-2-benzylphospholano)benzene (Formula 8, R=Bn, X=phen-1,2-diyl). Trans/trans 100%; $^{31}$P NMR (162 MHz, CDCl$_3$) δ −8.1 (s).

Example 20

Preparation of 1,2-Bis((1R,2R)-2-benzylphospholano)ethane (Formula 10, R=Bn, X=ethandiyl)

The titled compound was prepared by epimerizing 1,2-Bis ((1S,2R)-2-benzylphospholano)ethane (Formula 8, R=Bn, X=ethandiyl). Cis/trans:trans/trans=1:2.3; 4% of the cis/cis isomer remained unepimerized).

Example 21

Preparation of (1S,2S)-1-Phenyl-2-methylphospholaneborane (Formula 27)

27

(1S,2S)-1-Phenyl-2-methylphospholane was converted to its borane derivative, (1S,2S)-1-phenyl-2-methylphospholaneborane, for characterization purposes using a method similar to the procedure in Example 5. The resulting diastereoisomers were isolated as an oil, but were not separable via column chromatography over silica gel. Yield: 72% from (4R)-4-methyl-1,3,2-dioxathiepane 2,2-dioxide; $^1$H NMR (400 MHz, CDCl$_3$) δ 0.83 (m, 3 H), 1.27 (dd, J=16.36, 7.08 Hz, 3H), 1.62 (m, 1H), 1.86 (m, 1H), 2.20 (m, 5H), 7.46 (m, 3H), 7.68 (m, 2H); $^{13}$C NMR (101 MHz, CDCl$_3$) δ 14.40 (d, J=5.37 Hz), 26.18, 26.94 (d, J=38.39 Hz), 35.28 (d, J=35.32 Hz), 36.29 (d, J=6.91 Hz), 129.03 (d, J=9.98 Hz), 131.48, 131.73 (d, J=24.57 Hz), 131.67 (d, J=9.21 Hz); HRMS (EI): (M−BH$_3$+H)$^+$179.1136 ((M−BH$_3$+H)$^+$, exact mass calc'd for C$_{11}$H$_{16}$P: 179.0990).

Example 22

Preparation of (1S,2R)-1-Phenyl-2-(methoxymethyl)phospholane-sulfide (Formula 28)

28

(1S,2R)-1-Phenyl-2-(methoxymethyl)phospholane was converted to its phosphine sulfide derivative, (1S,2R)-1-phenyl-2-(methoxymethyl)phospholane-sulfide, for characterization purposes using a method similar to the procedure in Example 9. Column chromatography over silica gel (30% ethyl acetate in hexanes) provided a clear oil as a single diastereomer. Yield: 31% from (4S)-4-(methoxymethyl)-1,3,2-dioxathiepane 2,2-dioxide; bp 155.6° C.; $^1$H NMR (400 MHz, CDCl$_3$) δ 1.84 (m, 2H), 2.27 (m, 3H), 2.47 (m, 1H), 2.63 (m, 1H), 3.29 (s, 2 H), 3.56 (m, 1 H), 3.75 (m, 1 H), 7.48 (m, 3 H), 7.86 (m, 2 H); $^{13}$C NMR (101 MHz, CDCl$_3$) δ 25.11 (d, J=3.84 Hz), 30.41 (d, J=9.98 Hz), 36.84 (d, J=55.28 Hz), 43.33 (d, J=52.98 Hz), 59.20, 71.84 (d, J=4.61 Hz), 128.88 (d, J=11.52 Hz), 130.59 (d, J=10.75 Hz), 131.69 (d, J=3.07 Hz), 133.95 (d, J=71.40 Hz); $^{31}$P NMR (162 MHz, CDCl$_3$) δ 60.69 (s). Anal. Calc'd for C$_{12}$H$_{20}$BOP: C, 59.98; H, 7.13. Found: C, 59.321; H, 6.85.

Example 23

Preparation of (1S,2R)-1-Phenyl-2-benzylphospholane-borane (Formula 29)

29

(1S,2R)-1-Phenyl-2-benzylphospholane was converted to its borane derivative, (1S,2R)-1-phenyl-2-benzylphospholaneborane, for characterization purposes using a method similar to the procedure in Example 5. The product was isolated as a solid, which was recrystallized from ethyl acetate (15% in hexanes) to give the titled diastereomer. Yield: 61%; $^1$H NMR (400 MHz, CDCl$_3$) δ 1.02 (m, 3H), 1.65 (m, 1H), 1.80 (m, 1H), 2.14 (m, 4H), 2.47 (m, 1H), 2.81 (m, 1H), 3.12 (m, 1H), 7.16 (m, 5H), 7.44 (m, 3H), 7.64 (m, 2H); $^{13}$C NMR (101 MHz, CDCl$_3$) δ 26.00, 27.02 (d, J=39.16 Hz), 33.51 (d, J=6.91 Hz), 35.46 (d, J=6.91 Hz), 42.96 (d, J=33.01 Hz), 126.44, 128.57, 128.98, 129.09, 131.35 (d, J=2.30 Hz), 140.62 (d, J=12.28 Hz); $^{31}$P NMR (162 MHz, CDCl$_3$) δ 34.02 (s).

Example 24

Preparation of 1,2-Bis((1S,2S)-2-methylphospholanesulfide)-benzene (Formula 30)

30

1,2-Bis((1S,2S)-2-methylphospholano)benzene was converted to its phosphine sulfide derivative, 1,2-bis((1S,2S)-2-methylphospholanesulfide)benzene, for characterization purposes by reaction with sulfur (2.25 eq) in a manner similar to the procedure in Example 9. The resulting white solid was recrystallized from ethyl acetate (70% in hexanes) to provide the titled compound as a single diastereomer. Yield: 21% yield from (4R)-4-methyl-1,3,2-dioxathiepane 2,2-dioxide; $[α]^{20}_D$=−179.2° (c 1.0, CHCl$_3$); $^1$H NMR (400 MHz, CDCl$_3$) δ 1.54 (dd, J=17.95, 6.72 Hz, 6 H), 1.65 (m, 4H), 2.14 (m, 4H), 2.29 (m, 2H), 2.58 (m, 2H), 4.45 (m, 2H), 7.48 (m, J=1.71 Hz, 2 H), 7.64 (m, 2 H); $^{13}$C NMR (101 MHz, CDCl$_3$) δ 15.39, 24.30, 34.08, 37.11 (d, J=50.67 Hz), 38.88 (d, J=54.51 Hz), 131.21 (dt, J=8.64, 4.61, 4.41 Hz), 132.72 (dd, J=10.37 Hz), 139.60 (dd, J=66.41, 8.06 Hz); $^{31}$P NMR (162 MHz, CDCl$_3$) δ 67.39 (s); HRMS (EI): (M+H)$^+$343.0866 ((M+H)$^+$, exact mass calc'd for C$_{16}$H$_{25}$P$_2$S$_2$: 343.0873).

Example 25

Preparation of 1,2-Bis((1S,2R)-2-benzylphospholanoborane)benzene (Formula 31)

31

1,2-Bis((1S,2R)-2-benzylphospholano)benzene was converted to its bis-borane derivative, 1,2-bis((1S,2R)-2-benzylphospholanoborane)benzene, for characterization purposes, by reaction with BH$_3$·Me$_2$S (2 eq) in a manner similar to the procedure in Example 5. Recrystallization of the product from THF provided the titled compound as white crystals. Yield: 44% from (4S)-4-benzyl-1,3,2-dioxathiepane 2,2-dioxide as a single diastereomer; $[α]^{20}_D$=−99.4° (c 1.1, CHCl$_3$); $^1$H NMR (400 MHz, CDCl$_3$) δ 1.02 (m, 6H), 1.54 (m, 2H), 1.70 (m, 2H), 1.94 (s, 2H), 2.12 (m, 4H), 2.70 (s, 2H), 2.92 (s, 2H), 3.35 (m, 2H), 3.52 (s, 2H), 7.27 (s, 10 H), 7.49 (s, 2H), 7.63 (s, 2H); $^{13}$C NMR (101 MHz, CDCl$_3$) δ 25.72, 27.80 (d, J=33.78 Hz), 32.94 (d, J=7.68 Hz), 37.06 (d, J=5.37

Hz), 44.80 (d, J=33.78 Hz), 126.79, 128.95 (d, J=9.98 Hz), 130.37 (d, J=6.91 Hz), 133.19, 136.85 (d, J=6.14 Hz), 137.24 (d, J=5.38 Hz), 140.43 (d, J=13.82 Hz); $^{31}$P NMR (162 MHz, CDCl$_3$) δ 42.74 (s). Anal. Calc'd for C$_{28}$H$_{38}$B$_2$P$_2$: C, 73.40; H, 8.36. Found: C, 73.36; H, 8.61.

Example 26

Preparation of [Rh(1,2-Bis((1S,2R)-2-benzylphospholano)benzene)-(COD)]$^+$ OTf (Formula 19)

1,2-Bis((1S,2R)-2-benzylphospholano)benzene (200 mg, 0.465 mmol) was dissolved in THF (5 mL) and delivered drop wise with stirring to a solution of [Rh(COD)$_2$]$^+$ OTf$^-$ (211 mg, 0.451 mmol) in MeOH (5 mL). The metal solution turned from dark red to orange. The reaction was stirred for 45 minutes and then the volatiles were removed invacuo. The remaining orange paste was washed with ether and hexane producing an orange crusty solid. The product was dissolved in minimal THF. Addition of a small amount of hexane immediately produced small red crystals. The recrystallization medium was allowed to stand for two hours and then the solvent was removed with a pipette. The orange crystals were washed three times with hexane and the crystals were dried invacuo (224 mg). Yield: 61%; $^1$H NMR (400 MHz, CDCl3) δ 1.56 (m, 2H), 1.85 (m, 4H), 2.05 (m, 2H), 2.32 (m, 4H,) 2.54 (m, 8 H), 2.87 (m, 4H), 3.14 (m, 2H), 5.31 (d, J=102.33 Hz), 6.73 (d, J=7.08 Hz), 6.97 (m, 6 H), 7.44 (m, 2 H), 7.57 (m, 2 H); $^{13}$C NMR (101 MHz, CDCl$_3$) δ 14.06, 14.40 (d, J=5.37 Hz), 25.09 (d, J=36.08 Hz), 26.18, 26.94 (d, J=38.39 Hz), 35.08 (d, J=36.08 Hz), 35.27 (d, J=35.32 Hz), 36.11, 36.29 (d, J=6.91 Hz), 128.79 (d, J=9.21 Hz), 129.04 (d, J=9.98 Hz), 131.27 (d, J=2.30 Hz), 131.61 (d, J=46.07 Hz), 131.49 (d, J=2.30 Hz), 131.67 (d, J=9.21 Hz), 133.09 (d, J=8.44 Hz); $^{31}$P NMR (162 MHz, CDCl$_3$) δ 63.05 (d, J=148.33 Hz).

Determination of Isomeric Ratios of Phospholanes from Cyclization and Epimerization Cis:trans ratios of the monophospholanes (Formula 7 and Formula 9) were measured via integration of their respective $^{31}$P NMR signals. Cis/cis:cis/trans ratios were measured via integration of $^{31}$P NMR signals of either the free bisphospholanes after cyclization reactions (Formula 8) or corresponding sulfide or borane adducts (e.g., Formula 25 and 26). Similarly, cis/trans:trans/trans ratios were measured via integration of $^{31}$P NMR signals of either the free bisphospholanes after epimerization reactions (Formula 10) or corresponding sulfide or borane adducts (e.g., Formula 30 to 31). While cis/cis and trans/trans products of the cyclization and epimerization reactions were isolated and characterized, the cis/trans derivatives were not. However, the cis/trans derivatives were easily identified in $^{31}$P NMR spectra by observing two $^{31}$P NMR signals with equal coupling constants.

Assignment of Relative and Absolute Stereochemistry of Cyclized and Epimerized Products

All cis (Formula 7) and cis/cis (Formula 8) products were assigned by analogy to the relative and absolute stereochemistry of 1,2-bis((1R,2S)-2-methylphospholano)benzene, which was proven via the crystal structure of its bis-sulfide derivative (Formula 25). All trans and trans/trans products were assigned by analogy to the relative and absolute stereochemistry of (1S,2R)-1-phenyl-2-benzylphospholane, which was proven via the crystal structure of its borane derivative (Formula 29).

It should be noted that, as used in this specification and the appended claims, singular articles such as "a," "an," and "the," may refer to one object or to a plurality of objects unless the context clearly indicates otherwise. Thus, for example, reference to a composition containing "a compound" may include a single compound or two or more compounds.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patents, patent applications, and publications, are incorporated herein by reference in their entirety and for all purposes.

What is claimed is:

1. A method of making compounds of Formula 9, or Formula 10, or opposite enantiomers thereof, wherein
R is C$_{1-6}$ alkyl, halo-C$_{1-6}$ alkyl, C$_{3-8}$ cycloalkyl, halo-C$_{3-8}$ cycloalkyl, alkanoyl, C$_{1-6}$ alkoxy, C$_{1-6}$ alkoxy-C$_{1-6}$ alkyl, C$_{1-6}$ alkoxycarbonyl, aryl, aryl-C$_{1-6}$ alkyl, aryloxy, aryl-C$_{1-6}$ alkoxy, aryloxycarbonyl, aryl-C$_{1-6}$ alkoxycarbonyl, or carboxy, and each of the aryl and the C$_{3-8}$ cycloalkyl moieties are independently substituted or unsubstituted, and
X is C$_{1-12}$ alkyl, C$_{1-12}$ alkanediyl, or phen-1,2-diyl, in which phen-1,2-diyl is substituted or unsubstituted,
the method comprising epimerizing compounds of Formula 7, or Formula 8, or opposite enantiomers thereof, said epimerizing compounds of compounds of formula 7 or formula 8 at a temperature greater than or about equal to 100° C. and less than or about equal to the decomposition temperature of the compounds of Formula 7 or Formula 8, to give the compounds of Formula 9, or Formula 10, or the opposite enantiomers thereof, respectively, wherein R and X in Formula 7 and Formula 8 are as defined in Formula 9 and Formula 10.

2. The method of claim 1, wherein R is $C_{1-6}$ alkyl, $C_{1-6}$ alkoxy-$C_{1-6}$ alkyl, or aryl-$C_{1-6}$ alkyl, and X is $C_{1-6}$ alkyl, $C_{1-2}$ alkanediyl, or phen-1,2-diyl.

3. The method of claim 2, wherein R is methyl, ethyl, isopropyl, methoxymethyl, or benzyl, and X is methyl, methylene, ethanediyl, or phen-1,2-diyl.

4. The method of claim 1, further comprising epimerizing the compounds in the absence of oxygen.

5. The method of claim 1, wherein the amount of oxygen present in a reaction mixture containing the compounds of Formula 7, or Formula 8, or opposite enantiomers thereof, is less than about 1%, by mass.

6. The method of claim 1, wherein epimerizing the compounds comprises heating a reaction mixture containing the compounds of Formula 7, or Formula 8, or opposite enantiomers thereof, at a temperature greater than or about equal to 100° C. and less than or about equal to the decomposition temperature of the compounds of Formula 7 or Formula 8.

7. The method of claim 1, wherein epimerizing the compounds comprises heating a reaction mixture containing the compounds of Formula 7, or Formula 8, or opposite enantiomers thereof, at a temperature greater than or about equal to 100° C. and less than or about equal to 250° C.

8. The method of claim 7, wherein epimerizing the compounds comprises heating a reaction mixture containing the compounds of Formula 7, or Formula 8, or opposite enantiomers thereof, at a temperature greater than or about equal to 110° C., 120° C., 130° C., 140° C., 150° C., 160° C., 170° C., 180° C., 190° C., 200° C., 210° C., 220° C., 230° C., or 240° C.

9. The method of claim 7, wherein epimerizing the compounds comprises heating a reaction mixture containing the compounds of Formula 7, or Formula 8, or opposite enantiomers thereof, at a temperature less than or about equal to 110° C., 120° C., 130° C., 140° C., 150° C., 160° C., 170° C., 180° C., 190° C., 200° C., 210° C., 220° C., 230° C., or 240° C.

10. The method of claim 7, wherein epimerizing the compounds comprises heating a reaction mixture containing the compounds of Formula 7, or Formula 8, or opposite enantiomers thereof, at a temperature greater than or about equal to 140° C. and less than or about equal to 210° C.

11. The method of claim 7, wherein epimerizing the compounds comprises heating a reaction mixture containing the compounds of Formula 7, or Formula 8, or opposite enantiomers thereof, at a temperature greater than or about equal to 190° C. and less than or about equal to 210° C.

12. The method of claim 5 wherein the amount of oxygen present in the reaction mixture containing the compounds of Formula 7, or Formula 8, or opposite enantiomers thereof, is less than about 0.1% by mass.

13. The method of claim 12 wherein the amount of oxygen present in the reaction mixture containing the compounds of Formula 7, or Formula 8, or opposite enantiomers thereof, is less than about 0.01% by mass.

14. The method of claim 7, wherein epimerizing the compounds comprises heating a reaction mixture containing the compounds of Formula 7, or Formula 8, or opposite enantiomers thereof, at a temperature greater than or about equal to 130° C.

15. The method of claim 7, wherein epimerizing the compounds comprises heating a reaction mixture containing the compounds of Formula 7, or Formula 8, or opposite enantiomers thereog at a temperature greater than or about equal to 160° C.

16. The method of claim 7, wherein epimerizing the compounds comprises heating a reaction mixture containing the compounds of Formula 7, or Formula 8, or opposite enantiomers thereof, at a temperature greater than or about equal to 190° C.

17. The method of claim 7, wherein epimerizing the compounds comprises heating a reaction mixture containing the compounds of Formula 7, or Formula 8, or opposite enantiomers thereof, at a temperature greater than or about equal to 200° C.

18. The method of claim 7, wherein epimerizing the compounds comprises heating a reaction mixture containing the compounds of Formula 7, or Formula 8, or opposite enantiomers thereof, at a temperature less than or about equal to 230° C.

19. The method of claim 7, wherein epimerizing the compounds comprises heating a reaction mixture containing the compounds of Formula 7, or Formula 8, or opposite enantiomers thereof, at a temperature less than or about equal to 210° C.

20. The method of claim 7, wherein epimerizing the compounds comprises heating a reaction mixture containing the compounds of Formula 7, or Formula 8, or opposite enantiomers thereof, at a temperature less than or about equal to 190° C.

* * * * *